United States Patent [19]
LeBron

[11] Patent Number: 5,259,831
[45] Date of Patent: Nov. 9, 1993

[54] BACK BRACE AND BRACING METHOD

[76] Inventor: Rebecca A. LeBron, 575 Pearl St., Berea, Ohio 44017

[21] Appl. No.: 943,751

[22] Filed: Sep. 11, 1992

[51] Int. Cl.$^5$ .............................................. A61F 5/00
[52] U.S. Cl. ............................................ 602/7; 602/19
[58] Field of Search ........................................ 602/1-8, 602/19; 128/869-875

[56] References Cited

U.S. PATENT DOCUMENTS

| | | | |
|---|---|---|---|
| 3,680,548 | 8/1972 | Brown | 602/8 |
| 3,871,367 | 3/1975 | Miller | 602/19 |
| 5,016,624 | 5/1991 | Garrett | 602/7 |
| 5,074,288 | 12/1991 | Miller | 128/869 |
| 5,074,292 | 12/1991 | Cox | 602/7 |
| 5,158,531 | 10/1992 | Zamosky | 602/19 |

*Primary Examiner*—Michael A. Brown
*Attorney, Agent, or Firm*—Tarolli, Sundheim & Covell

[57] ABSTRACT

A method of bracing a patient's back includes constructing a back brace about the torso of the patient. The back brace includes a thermoplastic back panel and a thermoplastic chest panel. In the method, the back and chest panels are selected by size and are heat softened to render them manually pliable. The softened panels are pressed against the patient's back and chest, and are thus deformed into finished shapes in which they closely match the shapes of the patient's back and chest. The panels then rigidify in their finished shapes upon cooling to room temperature. The finished panels are mounted on the patient's back and chest by straps which attach the panels to each other in place on the patient.

6 Claims, 3 Drawing Sheets

5,259,831

BACK BRACE AND BRACING METHOD

FIELD OF THE INVENTION

The present invention relates to a brace for bracing a patient's back.

BACKGROUND OF THE INVENTION

A back brace including a back panel and a chest panel is known. The back panel has a contour matching the contour of the patient's back. The chest panel has a contour matching the contour of the patient's chest. The back panel and the chest panel are held in place against the patient's back and chest by a plurality of straps extending across the sides of the patient between the two panels.

SUMMARY OF THE INVENTION

The present invention is a method of bracing a patient's back by constructing a back brace about the torso of the patient. The back brace includes a back panel and a chest panel.

The method includes the step of providing a plurality of thermoplastic back panels, each of which has an inner side surface. The sizes of the inner side surfaces of the back panels differ from each other. A plurality of thermoplastic chest panels is also provided. The chest panels similarly have differently sized inner side surfaces.

The method further includes the steps of measuring the sizes of the back and the chest of the patient, and selecting back and chest panels for the patient. The selected back and chest panels are the ones which have inner side surfaces that correspond most closely in size to the measured sizes of the patient's back and chest, respectively.

The selected back and chest panels are heated to render them soft and pliable. When the back panel is in its softened condition, it is pressed against the patient's back. The back panel is thereby deformed into a finished shape in which its inner side surface has a contour matching the contour of the patient's back. The chest panel is similarly pressed against the patient's chest when it is in its softened condition. The chest panel is thereby deformed into a finished shape in which its inner side surface has a contour matching the contour of the patient's chest. The panels are then allowed to cool and rigidify in their finished shapes.

The finished panels are mounted on the patient's back and chest by a means for attaching them to each other in place on the patient. The back brace is thus constructed about the torso of the patient. As a result, the back and chest panels have shapes that closely match the shape of the patient's back and chest. The finished back brace therefore braces the patient's back effectively and comfortably.

BRIEF DESCRIPTION OF THE DRAWINGS

Further features of the present invention will become apparent to those skilled in the art to which the present invention relates from reading the following specification with reference to the accompanying drawings, in which.

DESCRIPTION OF A PREFERRED EMBODIMENT

Figure 1:
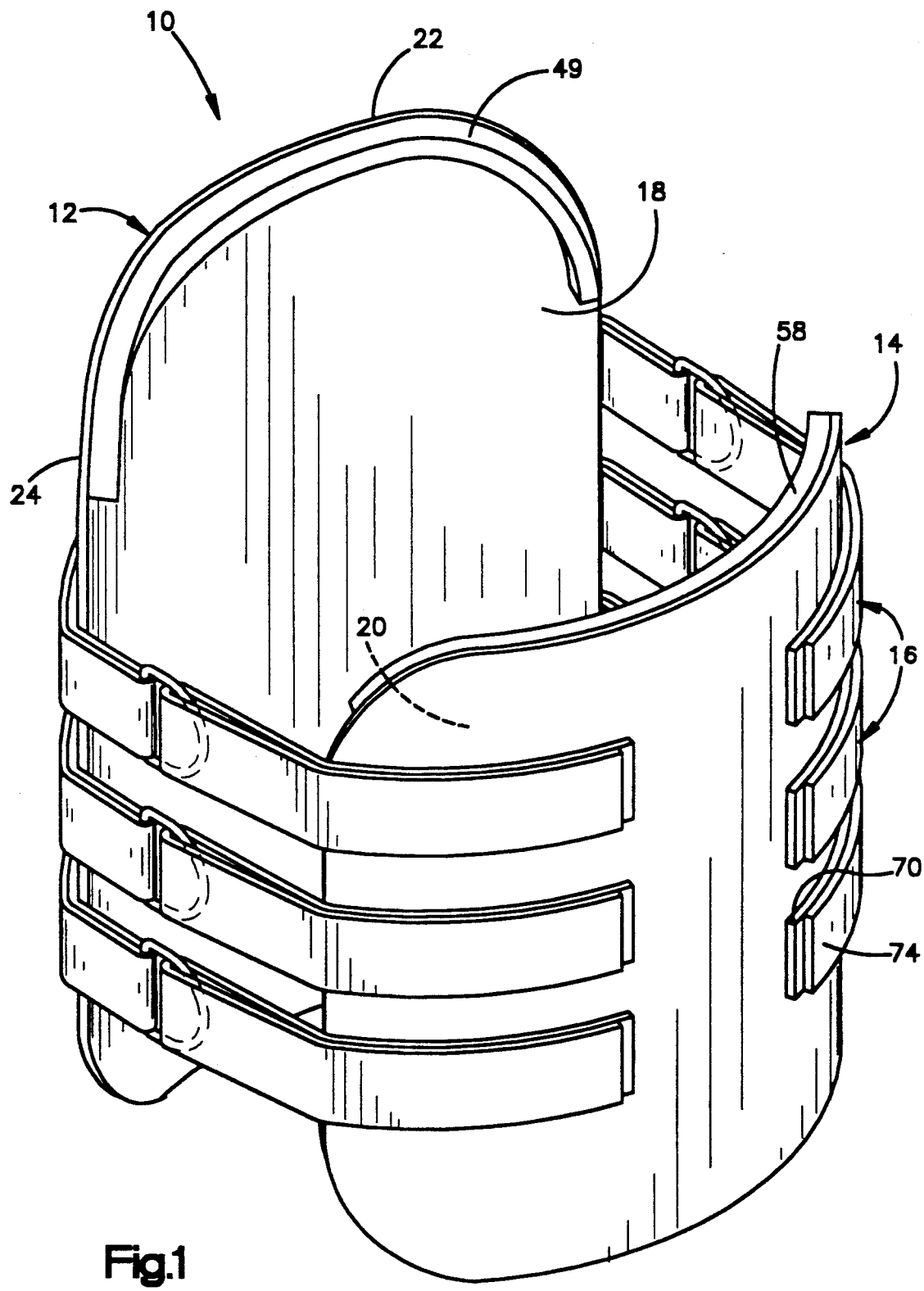
FIG. 1 is a perspective view of a back brace constructed in accordance with the present invention.

A back brace 10 constructed in accordance with the present invention is shown in FIG. 1. The back brace 10 comprises a back panel 12, a chest panel 14, and a plurality of straps 16. The back panel 12 has an inner side surface 18 with a contour matching the contour of an individual patient's back. The front panel 14 has an inner side surface 20 with a contour matching the contour of the patient's chest. When the straps 16 are in their fastening positions as shown in FIG. 1, they hold the back and chest panels 12 and 14 against the back and chest of the patient.

Figure 2:
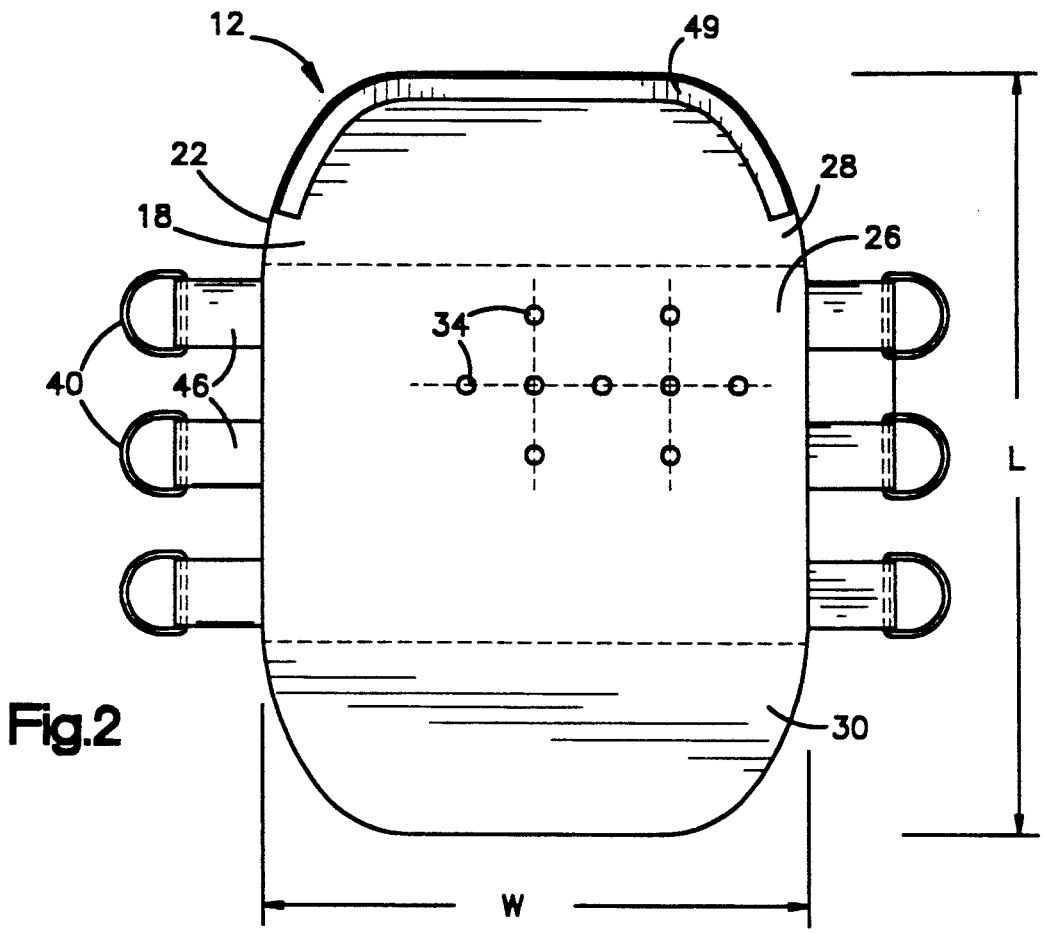
FIGS. 2 and 3 are inside and outside views of a part of the apparatus of FIG. 1.
Figure 3:
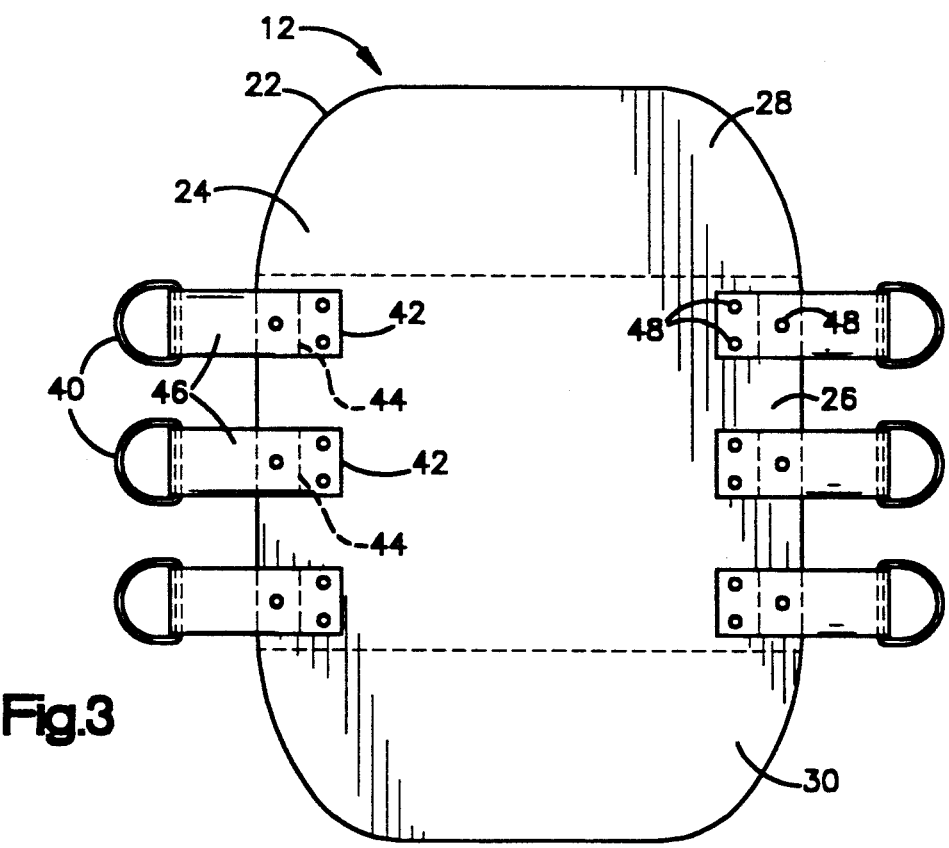

The back panel 12 has an initial condition as shown in FIGS. 2 and 3. When the back panel 12 is in its initial condition, the inner side surface 18 has a smooth planar contour. The back panel 12 also has a peripheral edge surface 22, and an outer side surface 24 (FIG. 3) which is coextensive with the inner side surface 18. In the preferred embodiment, the back panel 12 is elongated vertically and has three generally distinct portions. As indicated by dashed lines in the drawings, the three portions of the back panel 12 include a central portion 26, an upper end portion 28, and a lower end portion 30. The central portion 26 is substantially rectangular. Each of the upper and lower end portions 28 and 30 is generally semi-circular.

The back panel 12 further has a plurality of perforations 34. The perforations 34 extend through the back panel 12 between the inner and outer side surfaces 18 and 24. Preferably, each of the perforations 34 has a diameter of 3/16 inch and is spaced $\frac{1}{2}$ inch horizontally and vertically from each adjacent aperture 34. Such an array of the apertures 34 is shown partially in the drawings, and preferably extends over the entire back panel 12.

A plurality of metal D-rings 40 are mounted on the back panel 12. Each of the D-rings 40 extends through a loop between the opposite ends 42 and 44 of a respective flexible strap 46. Each of the straps 46 is fixed to the outer side surface 24 on the central portion 26 of the back panel 12 by aluminum fasteners 48. The straps 46 extend transversely outward beyond the peripheral edge surface 22. The D-rings 40 are thus located horizontally outward of the central portion 26 of the back panel 12. As shown in FIG. 2, a padding strip 49 is also mounted on the back panel 12 along the edge of the upper end portion 28.

Figure 4:
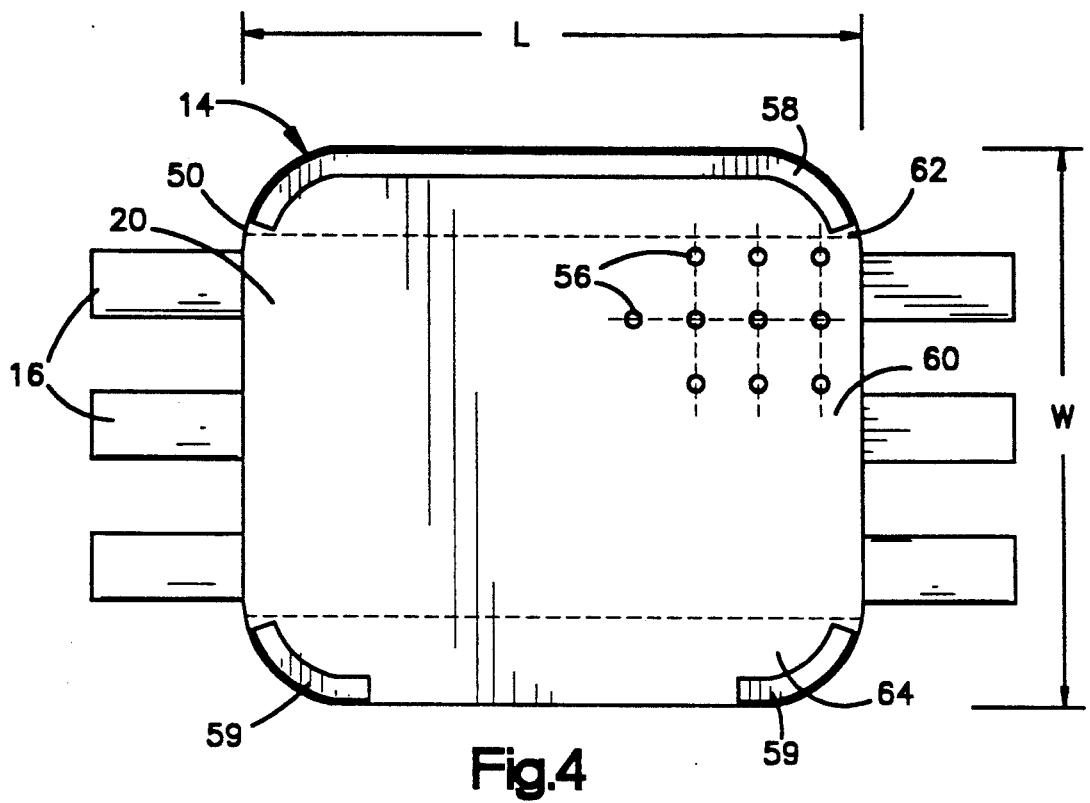
FIGS. 4 and 5 are inside and outside views of another part of the apparatus of FIG. 1.
Figure 5:
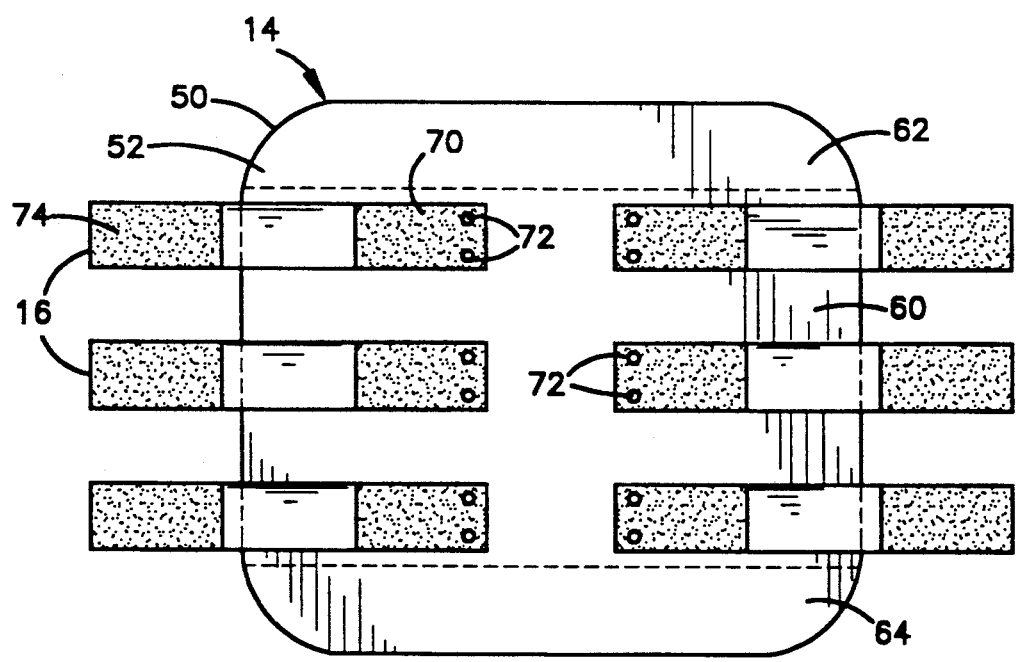

The chest panel 14 similarly has an initial condition as shown in FIGS. 4 and 5. Like the back panel 12, the chest panel 14 has a peripheral edge surface 50, an outer side surface 52 coextensive with the inner side surface 20, an array of perforations 56, and an upper padding strip 58. The chest panel 14 also has a pair of lower padding strips 59 for the patient's hips. The chest panel 14 has a substantially rectangular central portion 60 and two generally semi-circular vertical end portions 62 and 64. However, the chest panel 14 is preferably elongated horizontally rather than vertically.

The straps 16 are mounted on the chest panel 14. Specifically, each of the straps 16 has an inner end portion 70 which is fixed by aluminum fasteners 72 to the outer side surface 52 on the central portion 60 of the chest panel 14. The straps 16 extend longitudinally outward beyond the peripheral edge surface 50. Each of the straps 16 thus has an outer end portion 74 spaced horizontally from the inner end portion 70. As shown in FIG. 5, the inner and outer end portions 70 and 74 of each strap 16 have releasably engagable hook and eye surfaces such as those marketed with the trademark "VELCRO." Those surfaces are located on the sides of the straps 16 facing away from the outer side surface 52 of the chest panel 14.

The back and chest panels 12 and 14 are both formed of a thermoplastic material which is rigid at room temperature. One such material is marketed by Smith & Nephew Rolyan, Inc. with the trademark "SYNERGY SPLINTING."

In practice of the invention, individual back panels 12 are constructed in different sizes, as are individual chest panels 14. For example, a small size back panel 12 has a horizontal width W of 16 inches and a vertical length L of 22 inches. A large size back panel 12 has a horizontal width W of 18 inches an a vertical length L of 24 inches. A small size chest panel 14 has a horizontal length L of 18 inches an a vertical width W of 16 inches. A large size chest panel 14 has a horizontal length L of 22 inches and a vertical width W of 20 inches. The different sizes of the back and chest panels 12 and 14 are designed with reference to the anticipated sizes of patients who will wear the back braces 10. The back and chest panels 12 and 14 can therefore be constructed in any other useful size. The differently sized back and chest panels 12 and 14 are provided in a kit so that a single back bracing kit can accommodate a variety of differently sized patients.

The back brace 10 shown in FIG. 1 is preferably constructed about the patient's torso. The patient's back and chest are first measured. One of the differently sized back panels 12 is then selected with reference to the measured size of the patient's back. Specifically, the back panel 12 which has an inner side surface 18 that corresponds most closely to the measured size of the patient's back is selected. One of the differently sized chest panels 14 is selected on the same basis.

When a back panel 12 has been selected by size, it is softened and made pliable by the application of heat. Heat is preferably applied to the back panel 12 by submerging it in a warm water bath of approximately 160° F. This raises the temperature of the thermoplastic material to approximately 90°-100° F. The heated back panel 12 may then be allowed to cool to a lower temperature if necessary for it to be handled and held against the patient's back without causing discomfort.

While the heated back panel 12 remains pliable, it is pressed firmly against the patient's back, and is thus formed into the shape shown in FIG. 1. Specifically, pressure exerted manually against the outer side surface 24 of the back panel 12 causes the inner side surface 18 to be deformed into a shape in which it has the same contour as the patient's back. In the preferred embodiment of the invention, the back panel 12 is thin enough for the outer side surface 24 also to adopt the contour of the patient's back. The back panel 12 is then allowed to become rigid upon cooling to room temperature. The selected chest panel 14 is similarly heat softened, deformed, and cooled to a rigid state in which the inner and outer side surfaces 20 and 52 have contours matching the contour of the patient's chest.

After the back and chest panels 12 and 14 are shaped as described above, they are mounted in place against the back and chest of the patient by connecting them to each other with the straps 16, as shown in FIG. 1. Each of the outer end portions 74 of the straps 16 is threaded through an adjacent one of the D-rings 40, and is returned back over the respective inner end portion 70. The outer end portions 74 adhere releasably to the inner end portions 70. The tightness with which the back and chest panels 12 and 14 are held in place is adjusted accordingly. The back brace 10 is thus constructed about the torso of the patient.

In an alternative method, the back and chest panels 12 and 14 are mounted on the patient by the straps 16 before they are deformed fully into their final shapes. The straps 16 are then adjusted progressively as the panels 12 and 14 are deformed progressively in place on the patient. In either method, the finished back brace 10 has a shape which closely matches the shape of the patient's torso. The finished back brace 10 therefore braces the patient's back effectively and comfortably.

From the above description of the invention, those skilled in the art will perceive improvements, changes and modifications. Such improvements, changes and modifications within the skill of the art are intended to be covered by the appended claims.

Having described the invention, the following is claimed:

1. A method of bracing a patient's back, said method comprising the steps of:
   providing a plurality of thermoplastic back panels constructed in different sizes wherein each of said back panels having an inner side surface, the sizes of said inner side surfaces differing from each other;
   providing a plurality of thermoplastic chest panels constructed in different sizes wherein each of said chest panels having an inner side surface, the sizes of said inner side surfaces of said chest panels differing having a different size from each other;
   measuring the size of the back and size of the chest of the patient;
   selecting one of said back panels which has an inner side surface that corresponds most closely in size to the measured size of the patient's back;
   selecting one of said chest panels which has an inner side surface that corresponds most closely in size to the measured size of the patient's chest;
   applying heat to said selected back and chest panels to soften said selected back and chest panels;
   pressing said selected back panel against the patient's back when it is in its softened and pliable condition and thereby deforming said selected back panel into a finished shape in which said inner side surface of said selected back panel has a contour matching the contour of the patient's back;
   pressing said selected chest panel against the patient's chest when it is in its softened and pliable condition and thereby deforming said selected chest panel into a finished shape in which said inner side surface of said selected chest panel has a contour matching the contour of the patient's chest;
   allowing said selected back and chest panels to cool to room temperature when in said finished shapes;
   attaching said selected back panel in said finished shape releasably to said selected chest panel in said finished shape with a holding means for holding said attached panels releasably on the patient, wherein said holding means is adjustable to adjust the relative tightness with which said back panel in said finished shape and said chest panel in said finished shape are held on the patient.

2. A method as defined in claim 1 wherein each of said pressing steps includes the step of manually applying pressure to the respective one of said selected panels to deform it into its finished shape.

3. A method as defined in claim 1 wherein said pressing steps are carried out successively.

4. A method as defined in claim 1 wherein said pressing steps are carried out progressively while said selected panels are attached to each other and are held on the patient by said holding means.

5. A method as defined in claim 4 further comprising the step of progressively adjusting said holding means to adjust said tightness during said pressing steps.

6. A method as defined in claim 1 wherein said holding means comprises a plurality of adjustable straps extending across the sides of the patient connecting said back panel in said finished shape and said chest panel in said finished shape to each other, and further including the step of adjusting said plurality of adjustable strap to adjust the relative tightness with which said back panel in said finished shape and said chest panel in said finished shape are held on the patient.

* * * * *